US011588213B2

(12) United States Patent
Deininger et al.

(10) Patent No.: US 11,588,213 B2
(45) Date of Patent: *Feb. 21, 2023

(54) BATTERY CONNECTORS FOR IMPLANTABLE MEDICAL DEVICES

(71) Applicant: MEDTRONIC, INC., Minneapolis, MN (US)

(72) Inventors: Steven Deininger, Plymouth, MN (US); Jeffrey Clayton, Zimmerman, MN (US); Randy Roles, Elk River, MN (US); Darren Janzig, Center City, MN (US); Paul Eichstaedt, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 3 days.

This patent is subject to a terminal disclaimer.

(21) Appl. No.: 17/306,924

(22) Filed: May 3, 2021

(65) Prior Publication Data

US 2021/0257703 A1    Aug. 19, 2021

Related U.S. Application Data

(63) Continuation of application No. 16/273,122, filed on Feb. 11, 2019, now Pat. No. 11,011,801.

(51) Int. Cl.
*H05K 7/00* (2006.01)
*H01M 50/502* (2021.01)
(Continued)

(52) U.S. Cl.
CPC .......... *H01M 50/502* (2021.01); *A61N 1/378* (2013.01); *A61N 1/3754* (2013.01); *H01M 50/172* (2021.01); *H01M 50/543* (2021.01); *H01R 12/53* (2013.01); *H01R 12/58* (2013.01); *H01R 12/75* (2013.01)

(58) Field of Classification Search
USPC .......................... 361/728, 730, 752, 796, 800
See application file for complete search history.

(56) References Cited

U.S. PATENT DOCUMENTS 5,103,818 A   4/1992  Maston et al.
5,144,946 A   9/1992  Weinberg et al.
(Continued)

OTHER PUBLICATIONS

PCT/US2020/017613 International Search Report and Written Opinion, dated Apr. 28, 2020.

*Primary Examiner* — Hung S. Bui
(74) *Attorney, Agent, or Firm* — Withers & Keys, LLC

(57) ABSTRACT

Implantable medical devices that include a battery to power circuitry utilize a battery connector to electrically interconnect the battery to the circuitry. The battery connector may be mounted directly to a device housing to have the battery connector a fixed position within the device. Battery terminals of the battery are electrically connected to terminals on the battery connector, and the terminals on the battery connector are electrically connected to power terminals of the circuitry. The battery connector may include various features such as mounting grooves formed in a connector body, tapered pins to connect to power terminals on a circuit board, as well as plates to engage the battery terminals. The device housing may provide mounting features that allow the battery connector to be affixed directly to the device housing.

29 Claims, 11 Drawing Sheets

(51) Int. Cl.
   *A61N 1/375*    (2006.01)
   *A61N 1/378*    (2006.01)
   *H01R 12/53*    (2011.01)
   *H01R 12/58*    (2011.01)
   *H01R 12/75*    (2011.01)
   *H01M 50/172*   (2021.01)
   *H01M 50/543*   (2021.01)

(56) References Cited

U.S. PATENT DOCUMENTS

| | | |
|---|---|---|
| 5,314,451 A | 5/1994 | Mulier |
| 5,411,538 A | 5/1995 | Lin |
| 5,573,551 A | 11/1996 | Lin |
| 5,741,313 A | 4/1998 | Davis |
| 5,877,472 A | 3/1999 | Campbell et al. |
| 6,681,516 B2 | 1/2004 | Fayerman et al. |
| 7,003,356 B2 | 2/2006 | Tsukamoto et al. |
| 7,075,777 B2 | 7/2006 | Doffing |
| 7,337,002 B2 | 2/2008 | Gramse et al. |
| 7,527,535 B2 | 5/2009 | Mueller |
| 7,647,110 B2 | 1/2010 | Hornfeldt et al. |
| 7,713,656 B2 | 5/2010 | Zhao et al. |
| 7,751,893 B2 | 7/2010 | Biggs, Jr. et al. |
| 7,803,014 B2 | 9/2010 | Sprain et al. |
| 7,856,705 B2 | 12/2010 | Degieux et al. |
| 9,956,421 B2 | 5/2018 | Bunyan et al. |
| 10,003,063 B2 | 6/2018 | Aamodt et al. |
| 11,011,801 B2 * | 5/2021 | Deininger ............ H01M 50/552 |
| 2003/0040779 A1 | 2/2003 | Engmark et al. |
| 2008/0109044 A1 | 5/2008 | Gramse et al. |
| 2010/0187206 A1 | 7/2010 | Zhao et al. |
| 2015/0066114 A1 | 3/2015 | Bunyan et al. |
| 2015/0073247 A1 | 3/2015 | Gordon et al. |
| 2016/0260938 A1 | 9/2016 | Nielsen |
| 2016/0271401 A1 | 9/2016 | Klenner et al. |

* cited by examiner

BATTERY CONNECTORS FOR IMPLANTABLE MEDICAL DEVICES

TECHNICAL FIELD

Embodiments relate to battery connectors that interconnect a battery and circuitry of an implantable medical device.

BACKGROUND

Implantable medical devices that perform active functions such as stimulation therapy or physiological sensing utilize a battery and circuitry that is powered by the battery. The battery and the circuitry are mounted within a housing of the implantable medical device that isolates the circuitry from the body tissues and fluids surrounding the implantable medical device once implanted. The battery has anode and cathode terminals that must be electrically connected to corresponding anode and cathode terminals of the circuitry during device manufacturing.

One manner of electrically connecting the battery and circuitry involves including a battery connector that has electrical connections to both the battery and the terminals on a circuit board that includes the circuitry being powered. This indirect connectivity between the battery and circuit board may provide some benefits during device manufacture. For instance, the battery connector allows the relative positions of the battery and circuit board to be accommodated without requiring the battery to have terminals that extend to the terminals of the circuit board.

However, manufacturing difficulties may still arise when interconnecting the battery and circuit board with a battery connector. For instance, since the battery connector electrically connects to both the battery and to the circuit board, there are multiple electrical connections for a given electrical path that must align and connect correctly which presents a challenging manufacturing scenario. Other difficulties may also occur, such as attempting to bond a wire to a battery housing in order to connect the battery housing to a circuit board, lack of support for such electrical conductors extending between the battery and the circuit board, the inability to solder the battery's pins, and a lack of strain relief.

SUMMARY

Embodiments address these issues and others by providing a battery connector that affixes directly to a housing of the implantable medical device to provide a fixed location of the electrical terminals of the battery connector for connection to the battery and/or to the circuit board. Embodiments may include various other features in relation to the battery connector. Some embodiments may include a housing that is formed as multiple shells. Some embodiments may include a device housing defining protrusions where the battery connector mounts to the protrusions. Some embodiments may include a battery connector that has a groove where the groove is affixed to the device housing. Some embodiments may include a battery connector that utilizes a plate that is in contact with a battery housing. Some embodiments may include a battery connector that includes a conductive pin that extends to connect to a power terminal of a circuit board. Features such as these and others may additionally facilitate alignment of the pins to the circuit board, provide compatibility for soldering to the circuit board, provide strain relief between the battery and the circuit board, and so forth.

Embodiments provide an implantable medical device that includes a first enclosure and a circuit board fixed within the first enclosure and having first and second power terminals. The implantable medical device further includes a second enclosure that is coupled to the first enclosure and that comprises a first shell and a second shell that are bonded together. A battery that has a battery housing is positioned between the first shell and the second shell so as to be within the second enclosure, and the battery has battery terminal. A battery connector is positioned at the second enclosure and comprises a battery connector body that is affixed directly to the first shell and an electrical conductor affixed directly to the battery connector body. The electrical conductor is electrically coupled the first power terminal and to the battery terminal.

Embodiments provide an implantable medical device that includes a device housing defining at least one mounting protrusion and a circuit board fixed within the device housing and having first and second power terminals. A battery that has a battery housing is positioned within the device housing and has a battery terminal. The at least one mounting protrusion is electrically isolated from the battery terminal. A battery connector is positioned within the device housing and comprises a battery connector body that is affixed directly to the at least one mounting protrusion and at least one electrical conductor affixed directly to the battery connector body, the at least one electrical conductor being electrically coupled to the first power terminal and to the battery terminal.

Embodiments provide an implantable medical device that includes a device housing and a circuit board fixed within the device housing and having first and second power terminals. A battery that has a battery housing is positioned within the device housing and has a battery terminal. A battery connector is positioned within the device housing and comprises a battery connector body that has at least one linear groove that is affixed directly to the device housing. At least one electrical conductor is affixed directly to the battery connector body, and the at least one electrical conductor is electrically coupled to the first power terminal and to the battery terminal.

Embodiments provide an implantable medical device that includes a device housing and a circuit board fixed within the device housing and having first and second power terminals. A battery that has a battery housing is positioned within the device housing and has a battery terminal. A battery connector is positioned within the device housing and comprises a battery connector body that is affixed directly to the device housing. At least one electrical conductor is affixed directly to the battery connector body, the at least one electrical conductor being electrically coupled to the first power terminal and to the battery terminal. A conductive plate is coupled to the battery connector body and is in contact with the battery housing. A second electrical conductor is affixed directly to the battery connector body, and the second electrical conductor is electrically coupled to the conductive plate and to the second power terminal.

Embodiments provide an implantable medical device that includes a device housing and a circuit board fixed within the device housing and having first and second power terminals. A battery that has a battery housing is positioned within the device housing and has a battery terminal. A battery connector is positioned within the device housing and comprises a battery connector body that is affixed directly to the device housing; and at least one electrical conductor affixed directly to the battery connector body. The at least one electrical conductor is electrically coupled to the battery terminal and has a portion that forms a conductive pin that extends beyond the battery connector body and electrically couples to the first power terminal.

DETAILED DESCRIPTION

Embodiments provide implantable medical devices with a battery connector that electrically interconnects a battery with circuitry of the implantable medical devices. The battery connector may be mounted directly to the housing of the implantable medical device to establish a fixed relationship of the battery connector to the housing.

Figure 1:
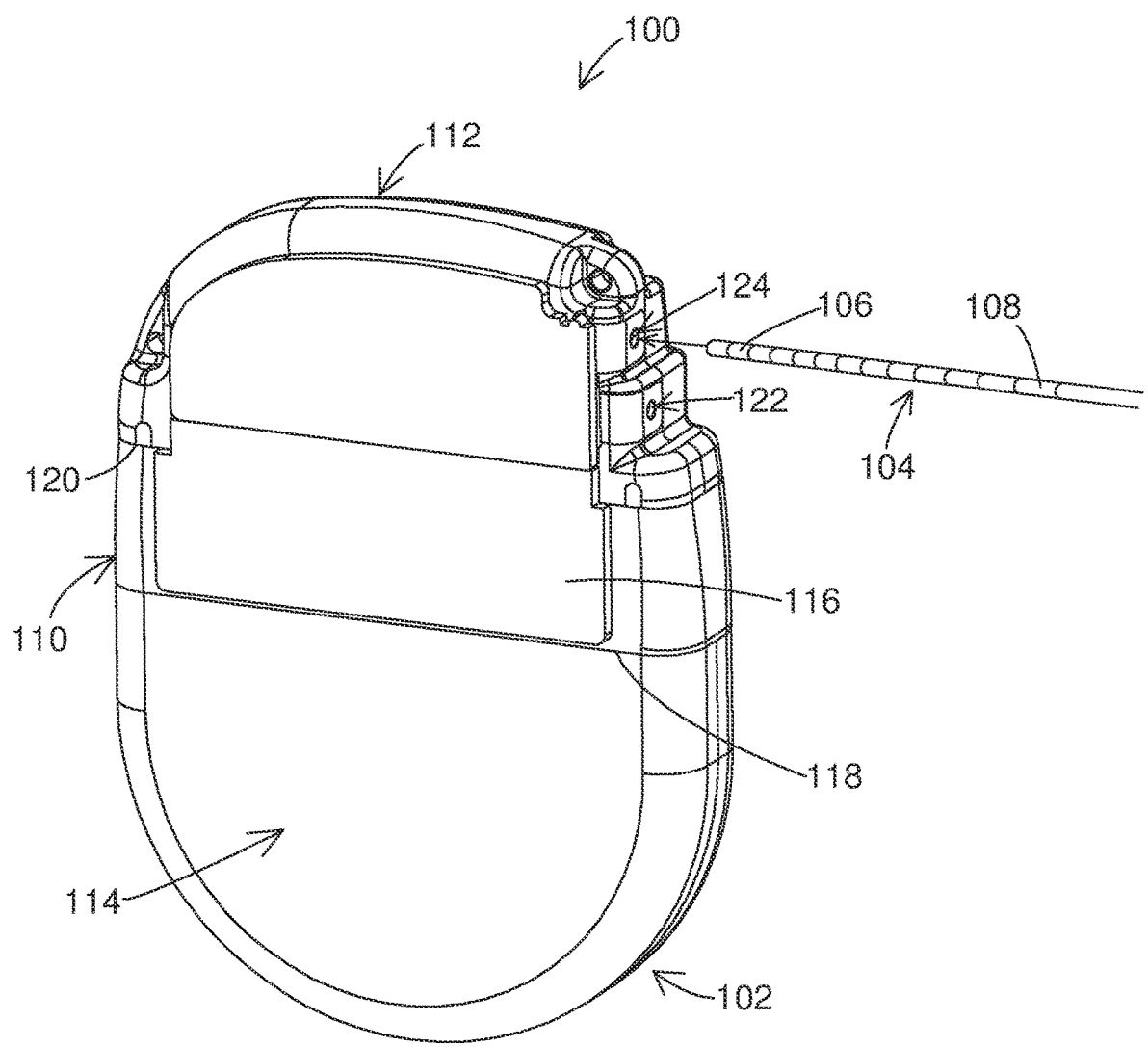
FIG. 1 shows an example of an implantable medical system that may include a battery connector.

FIG. 1 shows an example of an implantable medical system 100 that includes an implantable medical device 102 and one or more implantable medical leads 104. The implantable medical device 102 may be one of various types. For instance, the implantable medical device 102 may be an example of a neurostimulator such as those for deep brain, spinal cord, pelvic, or peripheral nerve sensing and/or stimulation.

This example of the implantable medical device 102 includes three sections, a circuitry enclosure section 110, a header section 112, and a battery enclosure section 114. It will be appreciated that these sections may be modular where the header section 112 mounts to the circuitry enclosure section 110 at a junction 120 and/or where the battery enclosure section 114 mounts to the circuitry enclosure section 110 at a junction 118. Alternatively, multiple of these sections may together be unitary in construction. In either case, together they form a complete device housing.

The header section 112 is affixed to or otherwise contiguous with the circuitry enclosure section 110. In one example where the header 112 is constructed of a polymer, the circuitry enclosure section 110 may include mounting barbs to which the header section 112 is molded. The header section 112 includes electrical connectors positioned within one or more lead bores 122, 124. The electrical connectors are electrically connected by feedthrough conductors or other electrical pathways to circuitry present within the circuitry section 110. When a proximal end of the lead 104 is inserted into a corresponding lead bore 122, 124, electrical contacts 106 present on the lead body 108 are electrically coupled to the electrical connectors. In this manner, signals may pass between the circuitry within the circuitry section 110 and distal electrodes located on a distal end of the lead 104, where conductors within the lead 104 carry the signals between the proximal contacts 106 and the distal electrodes.

The battery enclosure section 114 is also affixed to or otherwise contiguous with the circuitry enclosure section 110. As discussed in more detail below, according to this example, the battery enclosure 114 and the circuitry enclosure 110 may be constructed of metal such as but not limited to titanium, titanium alloys including grade 5 and grade 23, stainless steel including type 316, and the like and may be welded together at the junction 118. The battery enclosure section 114 includes the battery as well as any isolation materials that may be included to isolate the battery from the walls of the battery enclosure section 114, especially where the walls of the battery enclosure section 114 are conductive and it is not intended for the battery enclosure section 114 to be directly electrically connected to the battery.

The circuitry enclosure section 110 houses the electrical circuitry including circuit boards and the like necessary to provide the electrical functions of the implantable medical device 102. The circuitry may include a stimulation engine capable of producing stimulation pulses. The circuitry 114 may also or alternatively include a sensing circuit capable of receiving physiological signals.

The circuitry enclosure section 110 may be constructed of various materials such as may be constructed of metal such as but not limited to titanium, titanium alloys including grade 5 and grade 23, stainless steel including type 316, and the like. When the circuitry enclosure section 110 is metal or otherwise electrically conductive, the circuitry housed within the circuitry enclosure section 110 is separated from the walls of the circuitry enclosure section such as by non-conductive regions of the circuit board.

The circuitry enclosure section 110 may include various additional panels and coverings that allow access to internal portions of the circuitry enclosure section 110 during the manufacturing of the implantable medical device. For example, a panel 116 may be added after the electrical components are properly connected between the battery enclosure and circuitry enclosure sections. A similar panel may be provided on the header section 112 to allow access to the electrical components of the header section 112 during manufacturing. Additionally, a similar panel may be provided on the opposite side of the circuitry enclosure section 110 where such a panel provides access to a circuit board of the circuitry enclosure section 110 that is discussed in more detail below in relation to FIGS. 8 and 11. For any of these panels that contacts electrical conductors, the panel may be constructed of a non-conductive material, such as being formed from liquid silicon rubber. For any panels that do not contact electrical conductors, the panel may be constructed of a metal and then welded into position.

Figure 2:
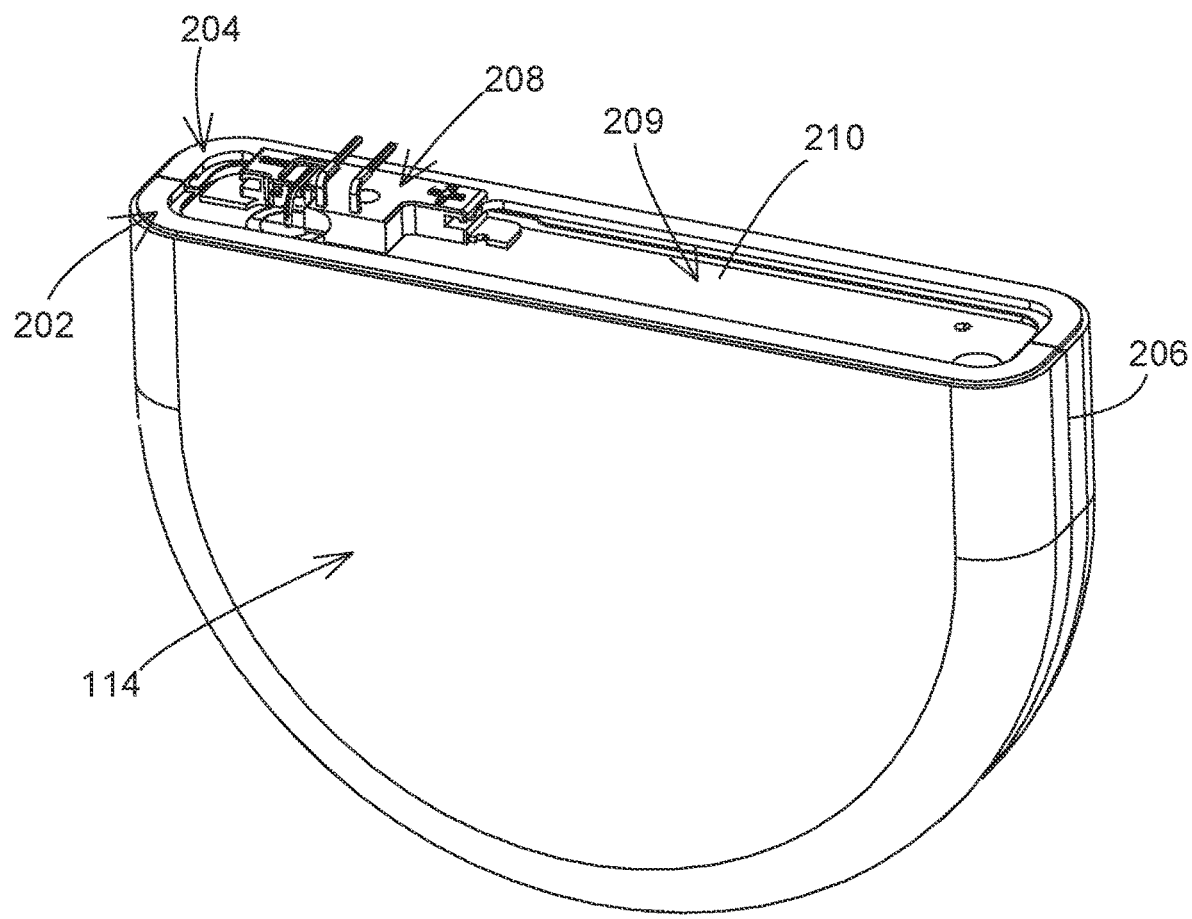
FIG. 2 shows an example of a power module of an implantable medical device that includes a battery connector.
Figure 7:
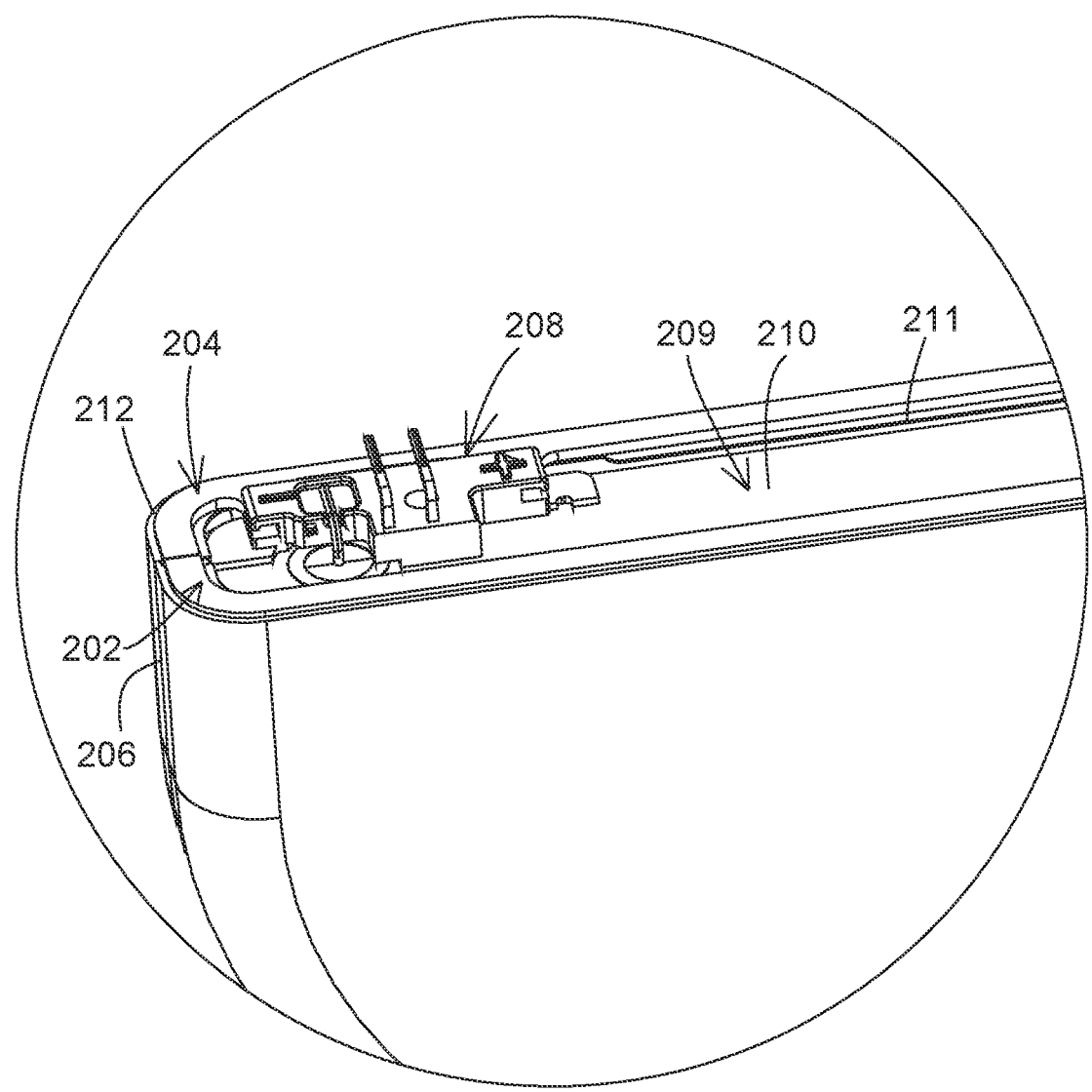
FIG. 7 shows an enlarged view of the power module to illustrate the electrical connections of the battery connector example to the battery.

FIG. 2 shows the battery enclosure section 114 to better illustrate the components. The battery enclosure section 114 of this example 114 includes first shell 204 and a second shell 202 that are joined together at a seam 206 to form the complete battery enclosure. A battery housing 210 that forms that outer surface of the battery 209 is present within the battery enclosure section 114 and may be positioned within an isolation cup constructed of a non-conductive material where the battery housing 210 is not electrically coupled to the battery enclosure 114. A battery connector 208 is also included and is electrically connected to the battery 209 while being affixed directly to the battery enclosure 114. FIG. 7 shows an enlarged view of the portion of the battery enclosure section 114 where the battery connector 208 is located.

Figure 3:
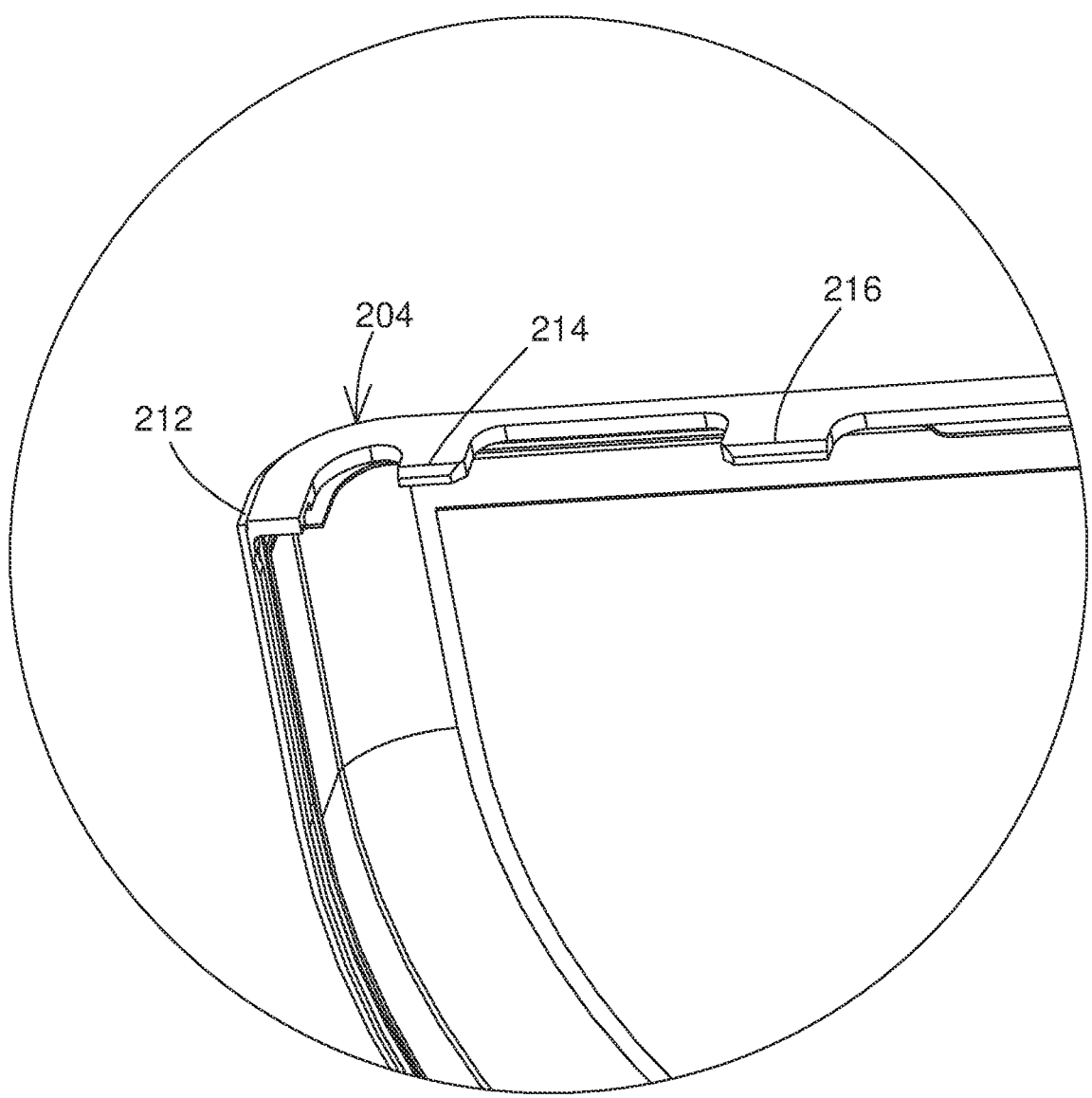
FIG. 3 shows mounting protrusions of a first housing shell of a battery enclosure.

FIG. 3 shows an enlarged view of the first shell 204. In this example, the first shell 204 includes mounting features that allow the battery connector 208 to be directly affixed to the shell 204. In this particular example, the mounting features are mounting protrusions 214, 216 that extend from the first shell 204. As discussed below, the battery connector 208 may include a connector body that includes features that mate to the mounting protrusions 214, 216. While two protrusions are shown in this example as the mounting features, it will be appreciated that any number of protrusions may be utilized to achieve the fixation of the battery connector 208 and the shape and size of the protrusions may vary from those shown.

FIG. 3 also shows a shelf 212 present around the periphery. The circuitry enclosure 110 may include an edge that rests on the shelf 212, and a weld may then affix the circuitry enclosure 110 to the shelf 212 to thereby fix the position of the circuitry enclosure 110 relative to the shelf 212 and therefore also to the battery connector 208.

Figure 4:
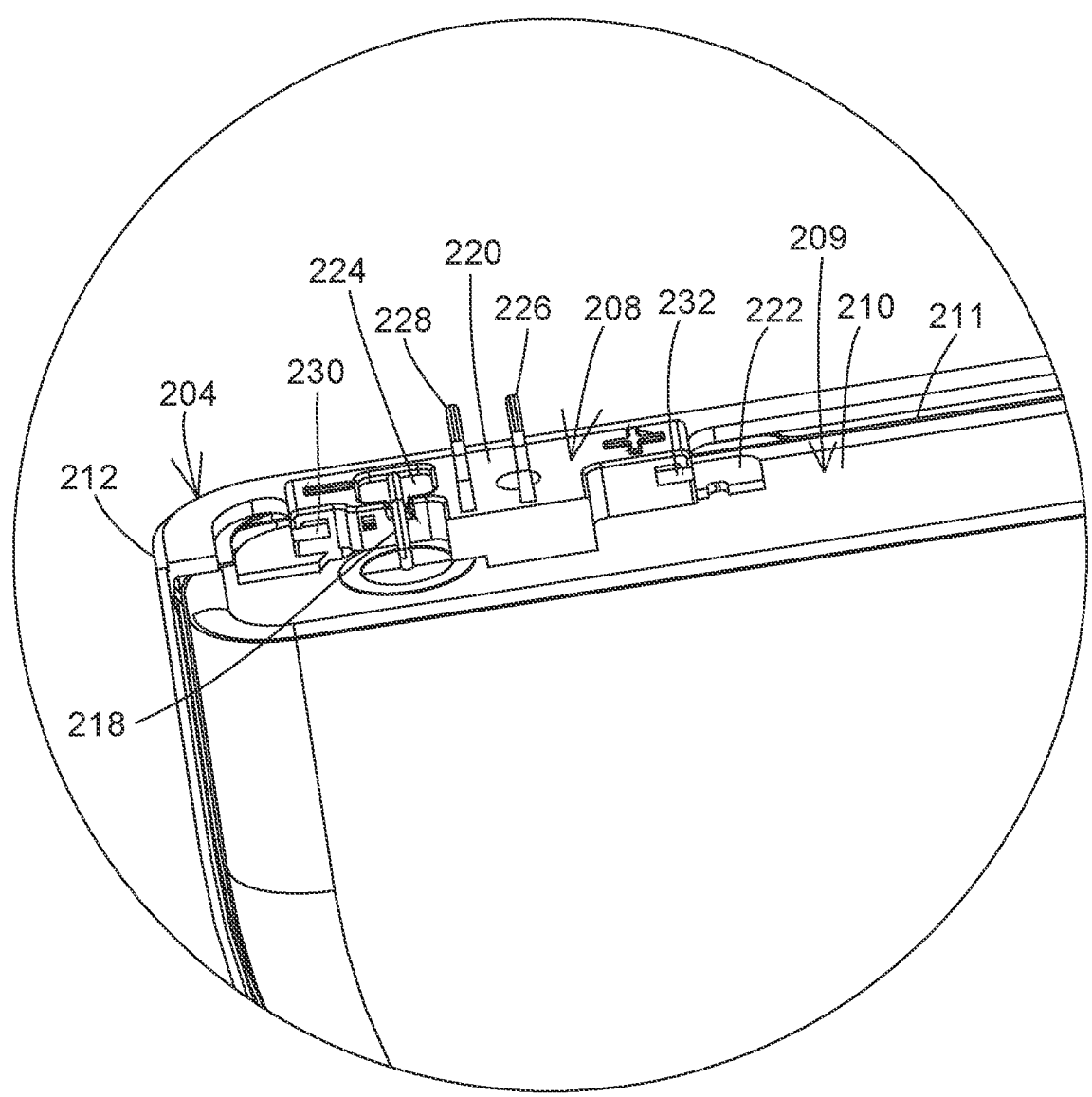
FIG. 4 shows the battery connector example being affixed to the first housing shell and also electrically coupled to the battery that is present within the first housing shell.

FIG. 4 shows the enlarged view of the first shell 204 once the battery connector 208 and the battery housing 210 have been installed. This view also shows that an isolation cup 211 is present on the battery housing 210 where half of the isolation cup 211 is present in the first shell 204 as shown in FIG. 4 while the other half is not shown but is present in the second shell 206. While the isolation cup 211 isolates the battery housing 210 from the shells 204, 206, the surface of the battery housing 210 that faces the battery connector 208 remains exposed. As discussed above, the isolation cup 211 may be present to electrically isolate the battery housing 210 from the battery enclosure 114 (FIG. 2) where the battery enclosure 114 is constructed of a conductive material but is not intended to be directly electrically connected to the battery housing 210. The isolation cup may be constructed of materials such as but not limited to polyimide, polyether ether ketone (PEEK), silicone, nylon, and the like.

Figure 5:
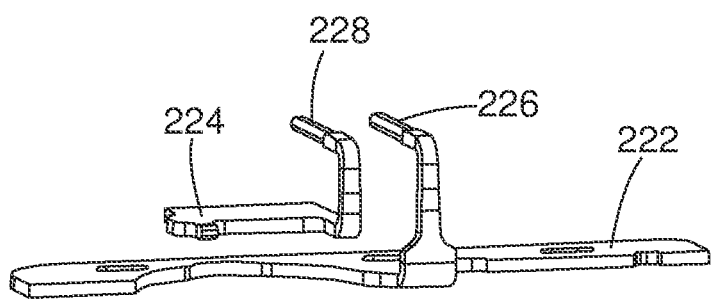
FIG. 5 shows conductive bodies of the battery connector example with a battery connector body removed for purposes of illustration.

As can be seen in FIG. 4, the battery connector 208 includes a non-conductive connector body 220 which may be constructed of various rigid non-conductive materials such as but not limited to polyetherimide, PEEK, liquid crystal polymer (LCP), polysulfone (PSU) and the like. In this example, multiple electrical conductors that pass through and are held in position by the connector body 220 include a first a conductive plate 222 coupled to a first conductive pin 226 and a second conductive plate 224 coupled to a second conductive pin 228. The connector body 220 thereby provides mechanical support for theses pins 226, 228 and plates 222, 224. The configuration and relative spacing of the pins 226, 228 and plates 222, 224 of this example can be seen in FIG. 5, where the connector body 220 is omitted for purposes of illustration.

In this example, both the plate and conductor pairings are present to provide electrical connectivity of both the cathode and anode terminals of the battery 209, where the battery housing 210 acts as one terminal and a battery terminal pin 218 acts as the other terminal. The battery housing 210 is electrically coupled to the conductive plate 222 and pin 226 while the battery pin 218 is electrically coupled to the conductive plate 224 and pin 228. The pin 218 may be welded to the plate 224 while the plate 222 may be welded to the battery housing 210.

Often, a battery 209 may have large tolerances for size and the specific position of the terminal pin 218. The presence of the battery connector 208 accounts for this variation in battery size as the battery terminal pin 218 does not need to directly engage a precise location of a power terminal on the circuit board of the circuitry enclosure section 110. Likewise, an additional conductor need not be added, either directly or indirectly to the battery, to extend from the housing 210 to a precise location of a terminal on the circuit board. Instead, the plate 224 is capable of receiving the pin 218 while the plate 222 achieves contact with the battery housing 210 even with variations in battery size, and the pins 226, 228 will already be in the proper position for engaging the power terminals of the circuit board. This connection of the pins 226, 228 to the circuit board is discussed in more detail below with reference to FIG. 8. Because of the length of the pins and the relatively compliant polymer construction of the body 220, the electrical connector also offers some strain relief between any movement of the battery 209 relative to the circuit board.

FIG. 4 also shows grooves 230 and 232 present within the connector body 208. These grooves 230, 232 may receive the corresponding mounting protrusions 214, 216 of the first shell 204 to affix the battery connector 208 to the first shell 204 and ultimately to the complete battery enclosure section 114. While the two grooves 230, 232 are shown, it will be appreciated that any number of grooves may be present to correspond to the number of mounting protrusions present on the battery enclosure section 114, and specifically on the first shell 204 of this example.

Figure 6:
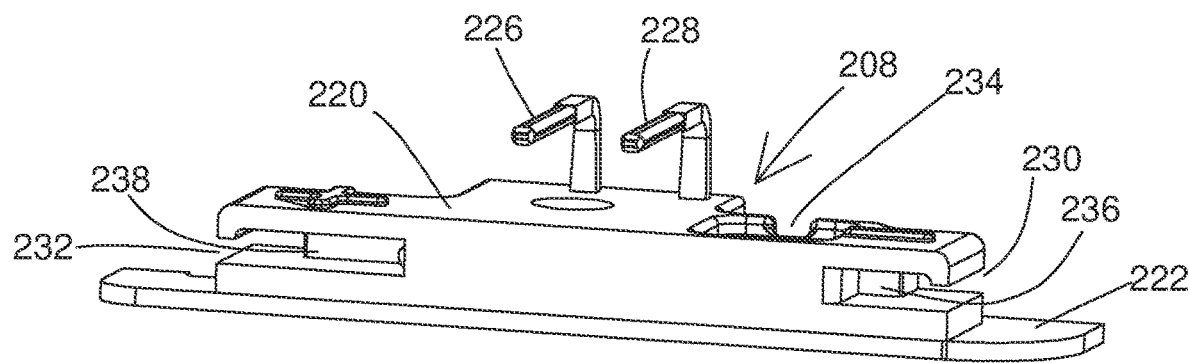
FIG. 6 shows a perspective view of the battery connector example.

The opposite view of the battery connector 208 is shown in FIG. 6 to illustrate that the grooves 230, 232 also include stops 236, 238 respectively. These stops 236, 238 set the position of the battery connector 208 relative to the first shell 204 by limiting the amount of ingress of the mounting protrusions 214, 216 into the grooves 230, 232. FIG. 6 also illustrates that the connector body 220 includes a valley 234 that allows the batter terminal pin 218 to easily pass through and reach the conductive plate 224.

The plates 222, 224 and pins 226, 228 may be constructed of various materials. The plates 222, 224 and pins 226, 228 conduct electrical current sourced by the battery 209 and therefore are constructed of conductive materials or are coated in a conductive material. Examples of suitable conductive materials for the plates 222, 224 and pins 226, 228 or coatings thereon include but are not limited to titanium, titanium alloys, niobium, and the like.

Conversely, the connector body 220 electrically isolates the conductive plate 222 and associated pin 226 from the conductive plate 224 and associated pin 228 as well as isolating the conductive plates 222, 224 and pins 226, 228 from the shell 204 to which the connector body 220 is attached. One manner of constructing the battery connector 208 is to mold the connector body 220 onto the pins 226, 228 and atop the plate 222 while molding underneath the plate 224 to thereby provide the connector body 220 between the plates 222, 224. Additionally, the connector body 220 may be over-molded directly onto the mounting features of the first shell 204 rather than sliding the body 220 onto the mounting features. Furthermore, the connector body 220 may be over-molded onto metal plates that are then welded to the mounting features of the first shell 204.

Figure 8:
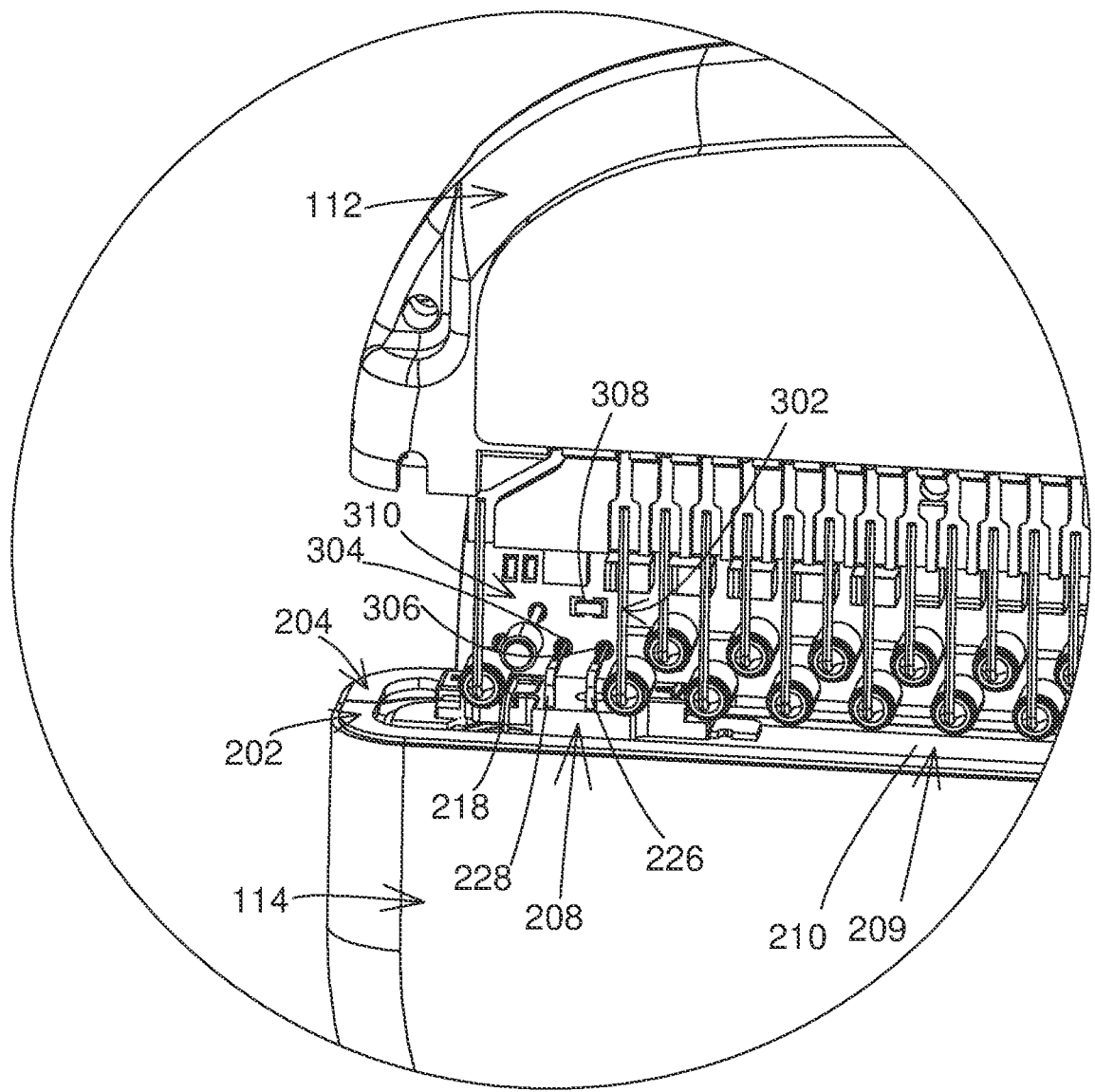
FIG. 8 shows a view of the implantable medical device example with a section of a device housing removed to illustrate the electrical connections of the battery connector example to a circuit board.

FIG. 8 shows the implantable medical device 102 with the housing of the circuitry enclosure section 110 removed to reveal the relationship of the battery enclosure section 114 and the battery connector 208 to the circuitry contained within the circuitry enclosure section 110. A circuit board 310 is present and hosts circuitry 308 including various circuit elements. The circuitry further includes feedthrough conductors 302 that pass signals from the circuit board 310 to the electrical connectors within the header 112.

The circuit board 310 includes power terminals 304, 306 for receiving the electrical power from the battery 209. The pin 228 of the battery connector 208 is present at the power terminal 304 while the pin 226 of the battery connector 208 is present at the power terminal 306. The battery connector 208, and hence the pins 226 and 228, has a well-defined position relative to the circuit board 310 due to the battery connector 208 being affixed to the battery enclosure section 114 in a precise location defined by the mounting protrusions 214, 216, which in turn is affixed to the circuitry enclosure section 110. Therefore, the pins 226 and 228 are necessarily in the proper position to mate to the power terminals 306, 304 respectively, upon joining the battery enclosure section 114 with the circuitry enclosure section 110.

Figure 9:
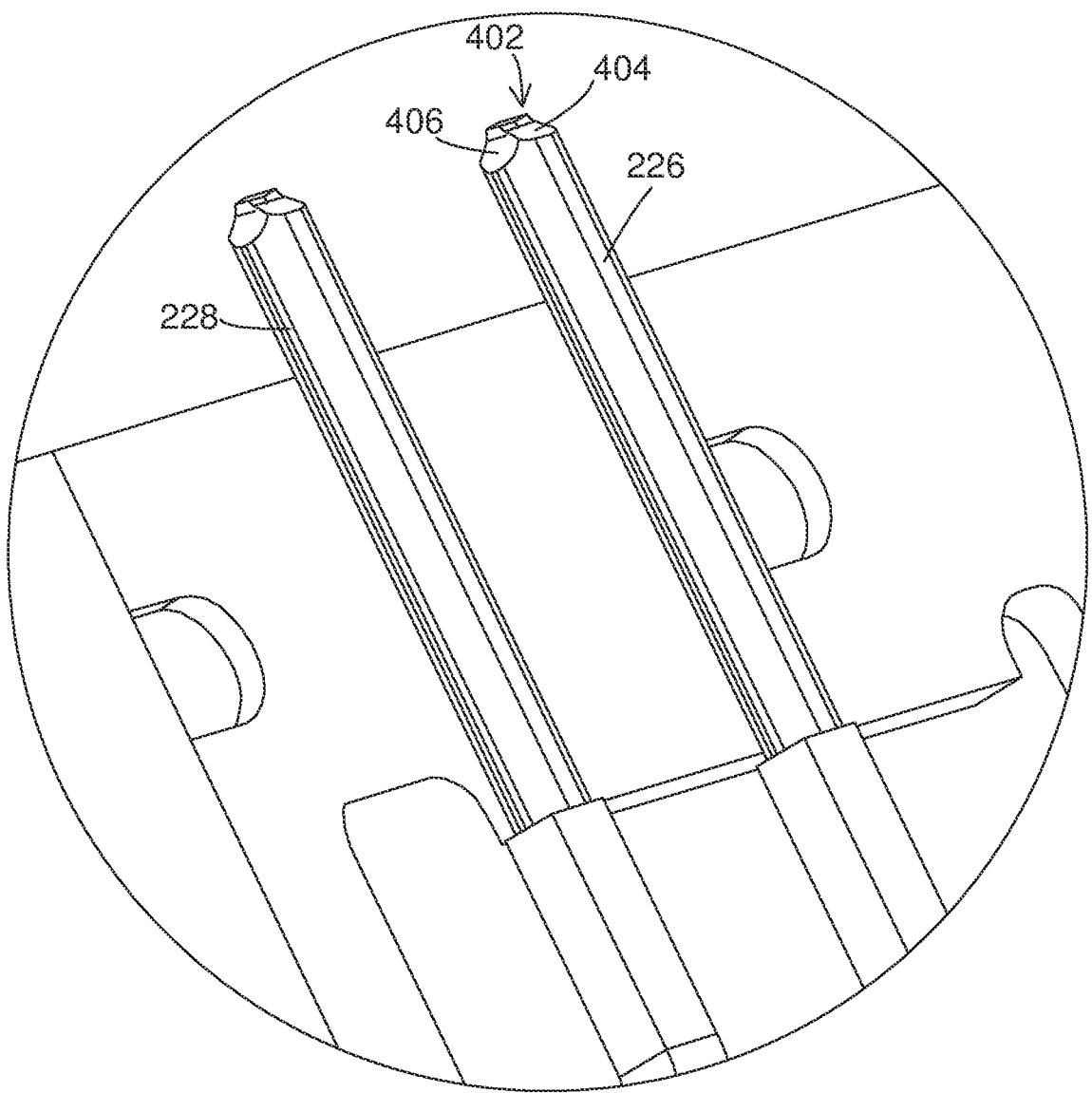
FIG. 9 shows an enlarged perspective view of conductive pins of the battery connector example.
Figure 10:
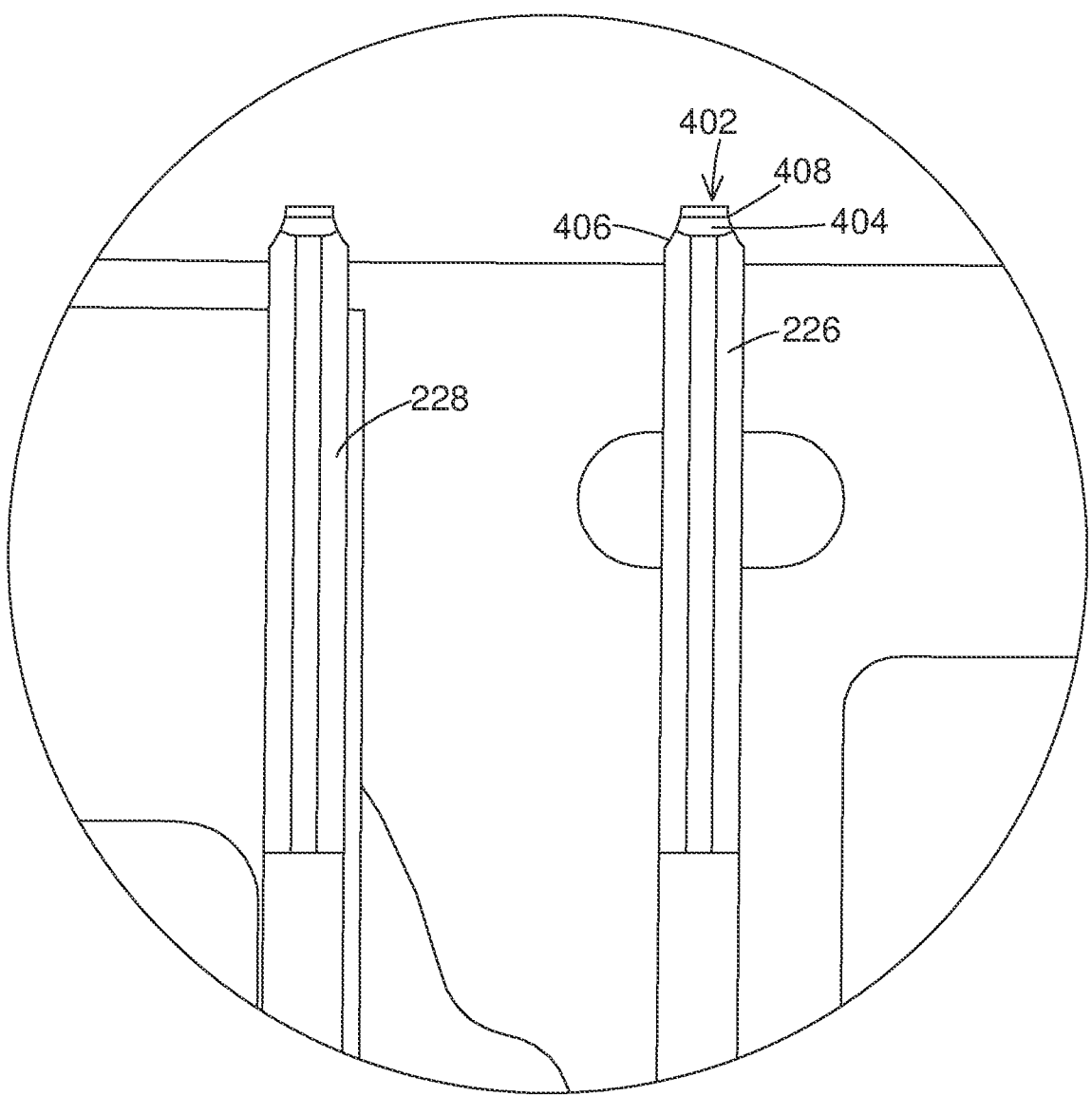
FIG. 10 shows an enlarged top view of conductive pins of the battery connector example.

To further aid in the pins 226, 228 engaging the power terminals 306, 304 of the circuit board 310 which are holes in this example, the pins 226, 228 may include tapered ends 402 as shown in FIGS. 9 and 10. As can be seen in FIG. 9, a taper 404 may be present on the top, with a corresponding taper on the bottom while a taper 406 may be present on a left side with a corresponding taper 408 on a right side as shown in FIG. 10. The tapers 404, 406, 408 assist in guiding the pins 226, 228 into the power terminal holes of the circuit board so that perfect alignment is not required.

The pins 226, 228 may be constructed of a metal that can be soldered or that can be plated in a metal that can be soldered, such as gold. This allows the pins 226, 228 to be soldered to the power terminals 306, 304 of the circuit board 310. In this way, the pins 226, 228 act as a transition metal where the battery terminal is constructed of a metal that cannot be soldered.

Figure 11:
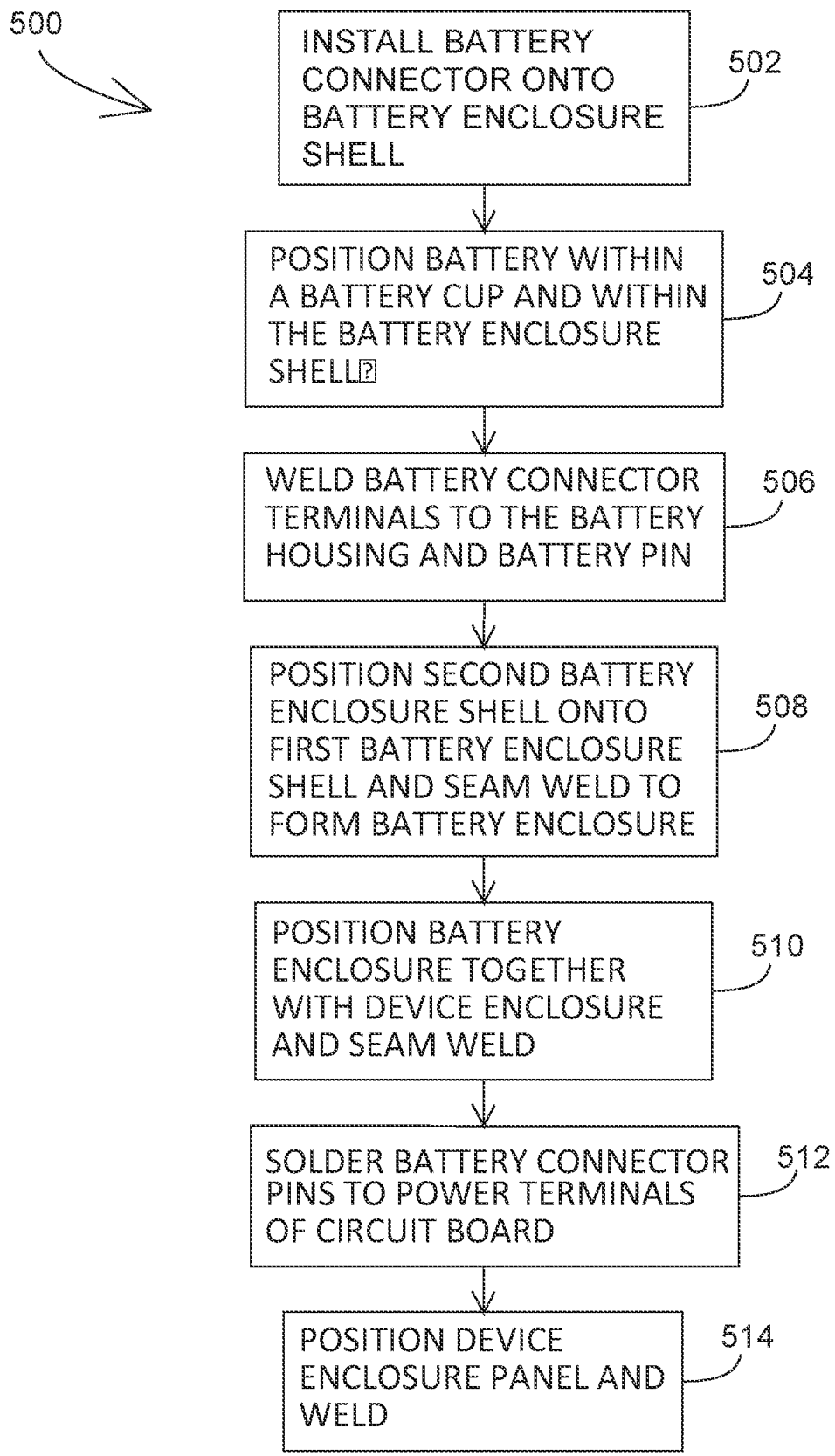
FIG. 11 shows an example of a manufacturing procedure to install the power module example.

FIG. 11 shows an example 500 of manufacturing steps that may be performed to construct the battery enclosure section 114 and to complete the assembly of the implantable medical device. In the example of FIG. 11, the battery enclosure portion 114 and circuitry enclosure portion 110 are modular and therefore initially separate but are brought together during the manufacturing steps. It will be appreciated that various aspects of the battery connector and related structures may also apply in other examples where the design is not modular, such as where a single, unitary housing is present for both the battery 209 and circuitry 308.

In this example of FIG. 11 where the enclosures are modular, the battery connector 208 is installed onto the shell 204 prior to the shell 204 being joined to the shell 202 at an operation 502. This makes introduction of the battery connector 208 relatively simple in that the battery connector 208 may be aligned and then press-fit with the grooves 230, 232 (FIG. 6) sliding onto the mounting protrusions 214, 216. As the shell 202 is not yet joined to the shell 204 and the battery 209 and cup 211 are not yet placed in the shell 202, there is no interference with positioning the battery connector 208.

The battery 209 is positioned within the cup 211 and the combination of the battery 209 and cup 211 are placed within the shell 204 at an operation 504. The battery 209 is positioned such that the battery terminal pin 218 is brought into alignment with the plate 224 and the battery housing 210 contacts the plate 222. At this point the battery connector terminals including the plate 222 and the plate 224 are welded to the battery housing 210 and the pin 218, respectively at an operation 506. The other shell 202 may then be positioned over the exposed side of the cup 211 where the seam 206 may then be welded to bond the shell 202 with the shell 204 and complete the battery enclosure section 114 at an operation 508.

At this point, the battery enclosure section 114 may be joined with the circuitry enclosure section 110 at an operation 510. The circuitry enclosure section 110 may already have the circuit board 310 installed such that the power terminals 304, 306 are present. As the battery enclosure section 114 is brought together with the circuitry enclosure section 110, the pins 226, 228 of the battery connector 208 are guided to the corresponding power terminals 304, 306. A seam weld may then be created at the junction 118 to bond the shells 202, 204 together with the circuitry enclosure section 110.

At this point, an access panel may not yet be installed onto the circuitry enclosure section 110 so that the opposite side of the circuit board 310 from that shown in FIG. 8 may be accessed. This allows the pins 226, 228 to be soldered to the power terminals 304, 306 at an operation 512. This panel may then be added, such as by welding the panel in place on the circuitry enclosure section 110 at an operation 514 where the panel is metal, to fully enclose the circuitry within the circuitry enclosure section 110. Any other panels as well as the header section 112 may be attached if not previously done to complete the implantable medical device 102.

While embodiments have been particularly shown and described, it will be understood by those skilled in the art that various other changes in the form and details may be made therein without departing from the spirit and scope of the invention.

What is claimed is:

1. An implantable medical device, comprising:
   a first enclosure;
   a circuit board fixed within the first enclosure and having a first power terminal;
   a second enclosure that is coupled to the first enclosure;
   a battery that has a battery housing, is positioned within the second enclosure, and has a battery terminal; and
   a battery connector positioned within the second enclosure and comprising:
      a battery connector body that is affixed directly to the second enclosure; and
      an electrical conductor affixed directly to the battery connector body, the electrical conductor comprising a pin portion being directly coupled to the first power terminal and a plate portion directly coupled to the battery terminal to electrically couple the first power terminal to the battery terminal.

2. The implantable medical device of claim 1, wherein the second enclosure includes an open top, wherein the battery connector body is affixed to the second enclosure at the open top.

3. The implantable medical device of claim 1, wherein the circuit board includes a second power terminal and the battery connector further comprises:
   a conductive plate that is coupled to the battery connector body and in contact with the battery housing; and
   a second electrical conductor affixed directly to the battery connector body, the second electrical conductor being electrically coupled to the conductive plate and to the second power terminal.

4. The implantable medical device of claim 1, wherein the second enclosure comprises at least one mounting feature and wherein the battery connector body is affixed directly to the at least one mounting feature.

5. The implantable medical device of claim 4, wherein the at least one mounting feature comprises multiple protrusions and wherein the battery connector body comprises multiple grooves that receive the multiple protrusions.

6. The implantable medical device of claim 1, wherein the second enclosure is constructed of a metal.

7. The implantable medical device of claim 6, further comprising a non-conductive battery cup positioned within the second enclosure with the battery being positioned within the non-conductive battery cup.

8. An implantable medical device, comprising:
a device housing defining at least one mounting protrusion;
a circuit board fixed within the device housing and having a first power terminal;
a battery that has a battery housing, is positioned within the device housing, and has a battery terminal, the at least one mounting protrusion being electrically isolated from the battery terminal; and
a battery connector positioned within the device housing and comprising:
a battery connector body that is affixed directly to the at least one mounting protrusion; and
at least one electrical conductor affixed directly to the battery connector body, the at least one electrical conductor being electrically coupled to the first power terminal and to the battery terminal.

9. The implantable medical device of claim 8, wherein the device housing comprises:
a first enclosure, wherein the circuit board is fixed within the first enclosure; and
a second enclosure, wherein the second enclosure has the at least one mounting protrusion and wherein the battery is positioned within the second enclosure.

10. The implantable medical device of claim 9, wherein the second enclosure is positioned externally of the first enclosure and the second enclosure abuts the first enclosure.

11. The implantable medical device of claim 10, wherein the second enclosure comprises a first shell bonded to a second shell.

12. The implantable medical device of claim 8, wherein the battery connector body comprises at least one groove that receives the at least one protrusion.

13. The implantable medical device of claim 8, wherein the circuit board includes a second power terminal and the battery connector further comprises:
a conductive plate that is coupled to the battery connector body and in contact with the battery housing; and
a second electrical conductor affixed directly to the battery connector body, the second electrical conductor being electrically coupled to the conductive plate and to the second power terminal.

14. An implantable medical device, comprising:
a device housing;
a circuit board fixed within the device housing and having a first power terminal;
a battery that has a battery housing, is positioned within the device housing, and has a battery terminal; and
a battery connector positioned within the device housing and comprising:
a battery connector body that has at least one linear groove that is affixed directly to the device housing; and
at least one electrical conductor affixed directly to the battery connector body, the at least one electrical conductor being electrically coupled to the first power terminal and to the battery terminal.

15. The implantable medical device of claim 14, wherein the device housing comprises:
a first enclosure, wherein the circuit board is fixed within the first enclosure; and
a second enclosure, wherein the battery is positioned within the second enclosure.

16. The implantable medical device of claim 15, wherein the second enclosure is positioned externally of the first enclosure and the second enclosure abuts the first enclosure.

17. The implantable medical device of claim 16, wherein the second enclosure comprises a first shell bonded to a second shell.

18. The implantable medical device of claim 14, wherein the device housing comprises at least one mounting feature and wherein the at least one linear groove receives the at least one mounting feature.

19. The implantable medical device of claim 18, wherein the at least one mounting feature comprises at least one protrusion.

20. The implantable medical device of claim 14, wherein the circuit board includes a second power terminal and battery connector further comprises:
a conductive plate that is coupled to the battery connector body and in contact with the battery housing; and
a second electrical conductor affixed directly to the battery connector body, the second electrical conductor being electrically coupled to the conductive plate and to the second power terminal.

21. An implantable medical device, comprising:
a device housing;
a circuit board fixed within the device housing and having a first power terminal;
a battery that has a battery housing, is positioned within the device housing, and has a battery terminal; and
a battery connector positioned within the device housing and comprising:
a battery connector body that is affixed directly to the device housing; and
at least one electrical conductor affixed directly to the battery connector body, the at least one electrical conductor being electrically coupled to the battery terminal and having a portion that forms a conductive pin that extends beyond the battery connector body and electrically couples to the first power terminal.

22. The implantable medical device of claim 21, wherein the pin has an end that has multiple opposing sloped sides, the end engaging the first power terminal.

23. The implantable medical device of claim 21, wherein the device housing comprises:
a first enclosure, wherein the circuit board is fixed within the first enclosure; and
a second enclosure, wherein the battery is positioned within the second enclosure.

24. The implantable medical device of claim 23, wherein the second enclosure is positioned externally of the first enclosure and the second enclosure abuts the first enclosure.

25. The implantable medical device of claim 24, wherein the second enclosure comprises a first shell bonded to a second shell.

26. The implantable medical device of claim 21, wherein the device housing comprises at least one mounting feature and the battery connector body is affixed directly to the at least one mounting feature.

27. The implantable medical device of claim 21, wherein the circuit board includes a second power terminal and the battery connector further comprises:
- a conductive plate that is coupled to the battery connector body and in contact with the battery housing; and
- a second electrical conductor affixed directly to the battery connector body, the second electrical conductor being electrically coupled to the conductive plate and to the second power terminal.

28. The implantable medical device of claim 27, wherein the battery connector has a portion that forms a second conductive pin that extends beyond the battery connector body and electrically couples to the second power terminal.

29. The implantable medical device of claim 28, wherein the second pin has an end that has multiple opposing sloped sides, the end of the second pin engaging the second power terminal.

* * * * *